(12) United States Patent
Mayer (10) Patent No.: US 9,309,605 B2
(45) Date of Patent: Apr. 12, 2016

(54) MONITORING LEVELER CONCENTRATIONS IN ELECTROPLATING SOLUTIONS

(71) Applicant: Novellus Systems, Inc., Fremont, CA (US)

(72) Inventor: Steven T. Mayer, Aurora, OR (US)

(73) Assignee: Novellus Systems, Inc., Fremont, CA (US)

( * ) Notice: Subject to any disclaimer, the term of this patent is extended or adjusted under 35 U.S.C. 154(b) by 717 days.

(21) Appl. No.: 13/711,254

(22) Filed: Dec. 11, 2012

(65) Prior Publication Data

US 2013/0161203 A1   Jun. 27, 2013

Related U.S. Application Data

(60) Provisional application No. 61/569,741, filed on Dec. 12, 2011.

(51) Int. Cl.
*C25D 21/14* (2006.01)
*G01N 27/26* (2006.01)

(52) U.S. Cl.
CPC .............. *C25D 21/14* (2013.01); *G01N 27/26* (2013.01)

(58) Field of Classification Search
CPC .................................. C25D 21/14; G01N 27/26
See application file for complete search history.

(56) References Cited

U.S. PATENT DOCUMENTS

| 4,324,621 | A  | 4/1982  | Kerby |
| 6,458,262 | B1 | 10/2002 | Reid et al. |
| 6,627,066 | B1 | 9/2003  | Isayama et al. |
| 6,740,221 | B2 | 5/2004  | Cheung et al. |
| 6,827,839 | B2 | 12/2004 | Sonnenberg et al. |

(Continued)

FOREIGN PATENT DOCUMENTS

| CA | 988879    | 5/1976  |
| CN | 2828067 Y | 10/2006 |

(Continued)

OTHER PUBLICATIONS

International Search Report and Written Opinion, dated Mar. 28, 2013, issued in Application No. PCT/US2012/069016.

(Continued)

*Primary Examiner* — Bryan D. Ripa
(74) *Attorney, Agent, or Firm* — Weaver Austin Villeneuve & Sampson LLP (57) ABSTRACT

Provided herein are methods and apparatus for determining leveler concentration in an electroplating solution. The approach allows the concentration of leveler to be detected and measured, even at very low leveler concentrations. According to the various embodiments, the methods involve providing an electrode with a metal surface, exposing the electrode to a pre-acceleration solution with at least one accelerator, allowing the surface of the electrode to become saturated with accelerator, measuring an electrochemical response while plating the electrode in a solution, and determining the concentration of leveler in the solution by comparing the measured electrochemical response to a model relating leveler concentration to known electrochemical responses. According to other embodiments, the apparatus includes an electrode, a measuring apparatus or an electrochemical cell configured to measure an electrochemical response, and a controller designed to carry out the method outlined above.

24 Claims, 6 Drawing Sheets

(56) References Cited

U.S. PATENT DOCUMENTS

| | | | |
|---|---|---|---|
| 7,144,488 | B2 | 12/2006 | Binstead et al. |
| 7,186,326 | B2 | 3/2007 | Shalyt et al. |
| 7,232,513 | B1 | 6/2007 | Webb et al. |
| 7,270,733 | B2 | 9/2007 | Wikiel et al. |
| 7,405,163 | B1 | 7/2008 | Drewery et al. |
| 7,449,098 | B1 | 11/2008 | Mayer et al. |
| 7,449,099 | B1 | 11/2008 | Mayer et al. |
| 7,531,079 | B1 | 5/2009 | Mayer et al. |
| 7,560,016 | B1 | 7/2009 | Mayer et al. |
| 7,776,741 | B2 | 8/2010 | Reid et al. |
| 7,799,200 | B1 | 9/2010 | Mayer et al. |
| 7,947,163 | B2 | 5/2011 | Mayer et al. |
| 8,268,154 | B1 | 9/2012 | Mayer et al. |
| 8,372,258 | B2 | 2/2013 | Willey et al. |
| 8,500,983 | B2 | 8/2013 | Ponnuswamy et al. |
| 2002/0074244 | A1* | 6/2002 | Sonnenberg ........... G01N 27/42 205/775 |
| 2004/0046121 | A1 | 3/2004 | Golden et al. |
| 2005/0183958 | A1 | 8/2005 | Wikiel et al. |
| 2008/0264801 | A1 | 10/2008 | West et al. |
| 2009/0057151 | A1 | 3/2009 | Shalyt et al. |
| 2009/0139873 | A1 | 6/2009 | Wang et al. |
| 2011/0025338 | A1* | 2/2011 | Willey ................... G01N 27/42 324/439 |
| 2011/0284386 | A1 | 11/2011 | Willey et al. |
| 2014/0367279 | A1 | 12/2014 | Brogan et al. |

FOREIGN PATENT DOCUMENTS

| | | |
|---|---|---|
| CN | 100337111 C | 9/2007 |
| JP | 2005-504965 | 2/2005 |
| KR | 10-2002-0060716 | 7/2002 |
| KR | 10-2006/0074593 | 7/2006 |
| KR | 10-2007-0012525 | 1/2007 |
| TW | 457544 B | 10/2001 |
| TW | 562877 B | 11/2003 |
| TW | 200409916 A | 6/2004 |
| TW | I226439 B | 1/2005 |
| WO | WO 03/279779 | 4/2003 |
| WO | WO 2006/110437 | 10/2006 |
| WO | WO 2011/017197 | 2/2011 |
| WO | WO 2013/090295 A1 | 6/2013 |

OTHER PUBLICATIONS

U.S. Appl. No. 13/572,483, filed Aug. 10, 2012, and titled "Selective Electrochemical Accelerator Removal," Mayer, et al.
U.S. Appl. No. 14/275,750, filed May 12, 2014, and titled "TSV Bath Evaluation Using Field Versus Feature Contrast," Brogan, et al.
US Office Action, dated Mar. 29, 2012, issued in 12/462,354.
US Notice of Allowance, dated Oct. 9, 2012, issued in 12/462,354.
PCT International Search Report and Written Opinion, dated Apr. 22, 2011, issued in PCT/US2010/043764.
PCT International Preliminary Report on Patentability and Written Opinion, dated Feb. 7, 2012, issued in PCT/US2010/043764.
Chinese First Office Action and Search Report dated Nov. 14, 2013, issued in CN 201080034658.4.
Chinese Second Office Action dated May 20, 2014, issued in CN 201080034658.4.
Taiwan Notice of Allowance and Search Report dated Oct. 24, 2013 issued in TW 099125629.
PCT International Preliminary Report on Patentability and Written Opinion, dated Jun. 17, 2014, issued in PCT/US2012/069016.

* cited by examiner

| Conc. (ml/L) | -0.46V Data | -0.47V Data | -0.46V Model Prediction | -0.47V Model Prediction | -0.46V Model % Error | -0.47V Model % Error |
|---|---|---|---|---|---|---|
| 0 | 235 | 522 | 0.06782 | 0.04877 | N/A | N/A |
| 0.125 | 143.3 | 225.2 | 0.12076 | 0.12247 | -3.39 | -2.02 |
| 0.25 | 73.8 | 115.8 | 0.29569 | 0.27652 | 18.28 | 10.61 |
| 0.5 | 53.8 | 77.3 | 0.50706 | 0.49105 | 1.41 | -1.79 |
| 1 | 42.8 | 55.8 | 0.83556 | 0.89147 | -16.44 | -10.85 |
| 2 | 35.3 | 42.4 | 1.49668 | 1.77119 | -25.17 | -11.44 |

MONITORING LEVELER CONCENTRATIONS IN ELECTROPLATING SOLUTIONS

CROSS REFERENCE TO RELATED APPLICATIONS

This application claims the benefit of U.S. Provisional Patent Application No. 61/569,741, titled "MONITORING LEVELER CONCENTRATIONS IN ELECTROPLATING SOLUTIONS", and filed Dec. 12, 2011, which is incorporated herein by reference in its entirety.

BACKGROUND

Damascene processing is a method for forming metal lines on integrated circuits. It is often used because it requires fewer processing steps than other methods and offers a high yield. Through-silicon-vias (TSVs) are sometimes used in conjunction with Damascene processing to create three-dimensional (3D) packages and 3D integrated circuits by providing interconnection of vertically aligned electronic devices through internal wiring. Such 3D packages and 3D integrated circuits may significantly reduce the complexity and overall dimensions of a multi-chip electronic circuit. Conductive routes on the surface of an integrated circuit formed during Damascene processing or in TSVs are commonly filled with copper.

A TSV is a vertical electrical connection passing completely through a silicon wafer or die. A typical TSV process involves forming TSV holes and depositing a conformal diffusion barrier and conductive seed layers, followed by filling of TSV holes with a metal. Copper is typically used as the conductive metal in TSV fill as it supports high current densities experienced at complex integration, such as 3D packages and 3D integrated circuits. Copper also supports high device speeds. Furthermore, copper has good thermal conductivity and is available in a highly pure state.

TSV holes typically have high aspect ratios which makes void-free deposition of copper into such structures a challenging task. Chemical vapor deposition (CVD) of copper requires complex and expensive precursors, while physical vapor deposition (PVD) deposition often results in voids and limited step coverage. Electroplating is a more common method of depositing copper into TSV structures; however, electroplating also presents a set of challenges because of the TSV's large size and high aspect ratio.

In a typical TSV electrofilling process, the substrate is negatively electrically biased and is contacted with a plating solution which generally includes copper sulfate or methane sulphonate as a source of copper ions, as well as sulfuric acid or copper methane sulfonic acid for controlling conductivity, along with chloride ions and organic additives in various functional classes, known as suppressors, accelerators and levelers. However, the use of standard electrolytes and additives, for example with concentrations and materials typically used for damascene plating, often results in very slow plating and in formation of voids during TSV filling. Further, filling of TSVs is usually accompanied by deposition of substantial amounts of copper in the field region during the lengthy plating period (10 to 100 minutes), which later need to be removed to isolate the individual features by chemical mechanical polishing (CMP) and/or other planarization or etching methods. Further, conformal filling, which includes deposition of substantial amounts of copper on the TSV sidewalls, can result in seam voids that may trap electrolyte and can lead to non-functional connections.

While existing methods address some of the problems associated with TSV filling, both faster filling methods, and methods with more robust control over the quality of the filling process within an individual wafer and over the course of plating multiple wafers on a plating tool, are desired.

SUMMARY

Some implementations described herein relate to methods, apparatus, and systems for plating a metal in features of a wafer substrate and monitoring the chemical composition of a plating bath. As noted, TSV applications involve plating copper in high aspect ratio vias (e.g., vias having aspect ratios of greater than about 10:1) with relatively large openings (e.g., at least about a 5 micrometer diameter). TSV structures are further described in U.S. Pat. No. 7,776,741 issued Aug. 17, 2010 and in U.S. patent application Ser. No. 13/110,488, titled "THROUGH SILICON VIA FILLING USING AN ELECTROLYTE WITH A DUAL STATE INHIBITOR", and filed May 18, 2011, each of which is herein incorporated by reference in its entirety. In implementations disclosed herein, the concentration of one or more leveler compounds in a plating bath is monitored using a technique and/or apparatus such as those exemplified herein.

In some implementations, a method of determining leveler concentration in a test solution is provided. The method may include providing an electrode having a metal surface, exposing the electrode to a pre-acceleration solution with at least one accelerator compound and allowing the surface of the electrode to become substantially saturated with the accelerator compound(s), measuring an electrochemical response while plating the electrode in a test solution with an unknown concentration of leveler, and determining the concentration of leveler in the test solution by comparing the measured electrochemical response to a model relating leveler concentration to known electrochemical responses. In certain embodiments, the electrode is a rotating disk electrode. While in certain implementations the electrode rotates between about 100-5000 rotations per minute while plating in the test solution, in other implementations the electrode rotates more than about 400 rotations per minute, for example 1600 rotations per minute. The electrode may be plated with metal in certain implementations, and in one embodiment the electrode is plated with copper. In other implementations the electrode is solid metal and is not otherwise plated before use.

The model relating leveler concentration to known electrochemical responses may be generated in certain embodiments by performing the method described above (providing an electrode with a metal surface, exposing it to a pre-acceleration solution until saturated, measuring an electrochemical response while plating in solution) with solutions having known leveler concentrations. The electrochemical response may be measured through galvanometric sweeping, stripping or AC impedance in certain embodiments. The electrochemical response measured may be a voltammetric or polarographic response. In certain implementations, measuring the electrochemical response may include polarizing the electrode with a constant current and measuring the electrode's potential over time. In other implementations, measuring the electrochemical response may include polarizing the electrode with constant potential and measuring the current to the electrode or the current density over time. In some embodiments, the pre-acceleration solution is between about 0.05 to 10 g/L accelerator compound in deionized water or weak acid. The accelerator compound may be selected from the group consisting of mercaptopropane sulfonic acid, dimercaptopropane sulfonic acid, mercaptoethane sulfonic acid, dimercaptoethane sulfonic acid, and DSP in certain implementations. The electrode may be plated in a pre-plating solution that includes the same species of metal ions as those present in the test solution. In certain embodiments, the pre-plating solution does not contain any leveler. In other embodiments, the pre-plating solution may contain leveler, but does not contain any leveler species which are the same as a leveler species whose concentration is sought to be characterized in the test solution. In further embodiments, the pre-plating solution may be a makeup solution of copper sulfate and acid, or a makeup solution of copper sulfate and chloride ions.

The method may further include rinsing the metal plated electrode with deionized water before exposure to the pre-acceleration solution. The method may also include rinsing the metal plated electrode before plating it in the test solution in order to remove unadsorbed accelerator compound. Furthermore, the method may include applying a current to the electrode during exposure to the pre-acceleration solution, where the current density is greater than about 5 mA/cm$^2$. In certain embodiments, the boundary layer thickness in the solution near the electrode when plating in the test solution is less than about 60 microns. The method may further include regenerating the electrode to its starting condition. This regeneration may be accomplished through a mechanical, chemical or electrochemical technique such as chemical etching or voltametric anodization. In certain embodiments the method is performed outside a primary plating apparatus, while in other embodiments the method is performed inside or substantially inside a primary plating apparatus. The method may be repeated in some implementations between about 1 and 10 times per day per test solution.

A further implementation of the method may include providing an electrode having a metal surface, exposing the electrode to a pre-acceleration solution with at least one accelerator compound, allowing the surface of the electrode to become substantially saturated with the at least one accelerator compound, providing a first solution with a known concentration of leveler and a second solution with an unknown concentration of leveler, preparing a third solution by adding an amount of the second solution to the first solution, measuring an electrochemical response while plating the electrode in the third solution, determining the concentration of leveler in the third solution by comparing the measured electrochemical response to a model relating leveler concentration to known electrochemical responses, and determining the concentration of leveler in the second solution by relating the known concentration of leveler in the first solution, the determined concentration of leveler in the third solution and the amount of second solution added to the first solution to make the third solution. The second solution may be a sample of solution taken from an electroplating apparatus. In certain implementations, the concentration of leveler in the second solution is determined by a controller programmed with instructions to calculate the concentration of leveler in the second solution based on the known concentration of leveler in the first solution, the amount of second solution added to the first solution to make the third solution, and the measured electrochemical response. The method may further include rinsing the electrode after exposure to the pre-acceleration solution to remove unadsorbed accelerator compound. In some implementations, two or more solutions used in the method may be provided in separate vessels. In other implementations, all of the solutions used in the method may be provided in a single vessel. The vessels may be provided on a conveyance mechanism. The vessels may be stationary in certain implementations. Where the vessels are stationary, the electrode is movable with respect to the vessels.

In another implementation, an apparatus for monitoring leveler concentrations in electroplating solutions is provided. The apparatus may include an electrode having a metal surface, one or more electrochemical cells configured to measure an electrochemical response of the electrode in solution as cathodic current is supplied to the electrode, and a controller configured to determine a concentration of leveler in the test solution based on a measured electrochemical response of the electrode. The controller may be designed or configured in certain embodiments to cause delivery of a defined current or potential to the metal plated electrode. In further embodiments, the controller may be designed or configured to cause one or more fluids to dispense into one or more vessels. In yet further embodiments, the controller may be designed or configured to adjust the level of leveler in an electroplating system by adding a dose of leveler to a plating solution in response to a determined concentration of leveler present in the test solution.

In a further implementation, an apparatus for monitoring leveler concentrations in electroplating solutions is provided. The apparatus may include an electrode having a metal surface, a measuring apparatus for measuring an electrochemical response of the electrode, and a controller designed or configured to determine a concentration of leveler present in a test solution by applying a measured electrochemical response of the electrode after the electrode is saturated with at least one accelerating compound and then plated in the test solution, to a model relating leveler concentration to known electrochemical responses. In certain implementations the controller may be designed or configured to cause delivery of a defined current or potential to the electrode. In further implementations, the controller may be designed or configured to cause one or more fluids to dispense into one or more vessels. The controller may also be designed or configured in certain embodiments to adjust the concentration of leveler in an electroplating system by adding a dose of leveler to a plating solution in response to a determined concentration of leveler present in the test solution. In some implementations the controller may be designed or configured to maintain a concentration of leveler in a plating solution within a defined range. In certain embodiments the defined range of leveler concentration is between about 1 and 1000 parts per million.

These and other features of the disclosed embodiments will be described in more detail below with reference to the associated drawings.

DETAILED DESCRIPTION

Introduction

In this application, the terms "semiconductor wafer," "wafer," "substrate," "wafer substrate," and "partially fabricated integrated circuit" are used interchangeably. One of ordinary skill in the art would understand that the term "partially fabricated integrated circuit" can refer to a silicon wafer during any of many stages of integrated circuit fabrication thereon. The following detailed description assumes the invention is implemented on a wafer. However, the invention is not so limited. The work piece may be of various shapes, sizes, and materials. In addition to semiconductor wafers, other work pieces that may take advantage of this invention include various articles such as printed circuit boards and the like.

The embodiments disclosed herein are not limited to any particular chemical or family of chemicals, but rather, are generally limited to compounds that one of ordinary skill in the art would recognize as leveler compounds (including any leveler compounds that are subsequently discovered or created). Chemicals may be characterized as leveler compounds based on the practical or engineering impact that the chemical has on the plating process. Plating leveler compounds can be generally described by their function and process sensitivities.

Addition of a leveling compound to a plating solution tends to increase the polarization (more specifically the surface electrochemical kinetic resistance) of the plating process. The polarization tends to selectively increase at regions where the concentration of leveler is greatest. Leveler compounds generally have a temporary impact (rather than a permanent one), requiring a continuous supply of the compound to the plating surface to maintain the leveler compound's polarizing influence. At typical leveler concentrations, the amount of polarization generally increases, (e.g., linearly) with an increase in the amount of leveler compound that reaches the surface. The compounds may be functional in their native form, or they may change in structure after being placed in the plating bath. Further, the leveler compound may be a precursor that reacts either chemically or electrochemically at the surface to create the functional polarizing kinetic suppressing agent.

The effectiveness and degree of polarization increase associated with leveling compounds are generally related to the specific concentration of the active species that reach the surface. Exposed or protruding regions of a surface tend to receive a greater supply of leveler than regions that are recessed or inaccessible. Leveling compounds may deactivate plating compounds that would otherwise have a catalytic impact on plating. In some cases a suppressing leveler compound or its active generated product are incorporated into a growing metal deposit, thereby removing the active material from the exposed plating surface. Without a continued supply of new leveling compound from the solution, the suppressing effect will diminish over time. Furthermore, regions of the surface that are exposed can have a greater flux of the leveler compound compared to recessed or otherwise inaccessible regions. Therefore, upon delivery of new leveling compound and removal of old leveling compound (e.g. through incorporation into the deposit) the exposed regions maintain a greater net level of suppression. Leveler compounds therefore generally can cause plating to occur at higher plating rates in recessed and inaccessible regions, and comparatively lower plating rates in exposed regions. Furthermore, leveler compounds may also terminate or slow the growth of highly accelerated or catalyzed regions of a plating surface such as protrusions containing relatively high concentrations of accelerator.

Leveler compounds often contain one or more nitrogen, amine, imide or imidazole functional groups, and may also contain sulfur functional groups. In some instances, leveler compounds also have surfactant-like properties. Copper plating leveler compounds may include one or more five and six member rings and conjugated organic compound derivatives. Many leveler compounds contain one or more nitrogen groups that are part of the ring structure. The compound may further contain ethoxide groups, such as a general backbone similar to polyethylene glycol or polyethylene oxide, with fragments of amine functionally inserted over the large chain. A specific example of this chemical class of compounds is Janus Green B.

Leveling agents may be polymeric or monomeric/non-polymeric. Examples of some polymeric leveling agents include polyethylenimine, polyamidoamines and reaction products of an amine with various oxygen epoxides or sulfides. An example of a diffusion-controlled non-polymeric leveling compound that incorporates a copper plating compound is the sulfur-containing 6-mercapto-hexanol. The compounds, particularly those that are amines, may be primary, secondary or tertiary alkyl amines. They may also be aryl amines or heterocyclic amines. Examples of amines include, but are not limited to, dialkylamines, trialkylamines, arylalkylamines, triazoles, imidazole, triazole, tetrazole, benzimidazole, benzotriazole, piperidine, morpholines, piperazine, pyridine, oxazole, benzoxazole, pyrimidine, quonoline, and isoquinoline. Imidazole and pyridine may be especially useful. Example epoxides include, but are not limited to, epihalohydrins such as epichlorohydrin and epibromohydrin, and polyepoxide compounds. Particularly suitable polyepoxide compounds are those having two or more epoxide moieties joined together by an ether-containing linkage. However, as noted and described above, a leveling compound does not need to have any particular chemical compounds or structure. Rather, in relation to this disclosure, a leveling compound may be characterized at least in part by its electrochemical function and impact. Leveling compounds are further discussed and described in US Patent Publication No. 2009/0139873, which is herein incorporated by reference in its entirety.

Disclosed embodiments maintain reliability of the plating feature filling operation for TSV and Damascene filling by allowing measurement of a leveler, particularly at very low leveler concentrations, in a plating solution. The concentration of leveling compounds, particularly those used in TSV plating operation, can be very low (e.g., 1-2 ppm or lower). The concentration of leveler should be low to avoid terminating the bottom-up growth process that occurs over typical processing times of about 10 to 100 minutes. If the concentration of leveler is too high, it will tend to shut down the superfilling mechanism generally associated with the geometric concentration mechanism of accelerating compounds at the base of the growing TSV. This is a mechanism by which a suppressor additive (e.g., a polyethylene oxide-polypropylene oxide) preferentially suppresses electroplating in field regions during initial stages of plating and an accelerator promotes filling within feature recesses throughout the plating process. However, if the concentration or activity of leveler is too low, over very long periods of plating a deep TSV feature (typically 10 to 100 minutes) the surface can slowly depolarize as the accelerator in the bath reacts at the plating surface. As mentioned above, levelers often have a dual functional role of both (1) creating suppression and (2) removing the catalytic effect of the accelerating compound. Thus, maintaining a low, consistent concentration of leveler in the plating solution is especially useful in electrodepositing metals. Further, because leveler compounds are typically consumed, incorporated, or have a relatively short active life, accurate measurement of leveler compound concentrations is needed to maintain constant plating conditions while continuously and sequentially plating a large number of wafers.

Various techniques may be employed for measuring plating bath components, including levelers. These include various methods employing analysis of cycling voltammetry in combination with various chemical titrations, HPLC, and spectrophotometric measurement.

Low leveler concentrations (as used herein low concentration means ppb (parts per billion) to a few ppm (parts per million)) in copper plating baths, particularly copper plating baths for large and deep TSV structures, are instrumental in controlling and creating optimal fill performance and maintaining bath performance (longevity/stability). However, because the concentration of leveler is typically so low, the electrochemical influence of the leveler in the bath is subtle and occurs over long periods of time, thereby making detection by current methods (e.g., CVS voltammetry, titration, spectroscopy) and quantification/determination of the concentration very difficult. The method and associated hardware disclosed herein provide a low cost, highly accurate approach to measuring leveler concentration, which is particularly suited for (but not limited to) very low leveler concentrations.

Certain plating baths that contain additives having multiple functional or operative roles in the bath have been found useful in high-rate bottom-up TSV feature filling (vs. "V" TSV feature filling). These baths are sometimes referred to as two-component plating baths, and they generally contain a strong polyethylene oxide (PEO), polyproplyene oxide (PPO), polyethylene glycol (PEG) and/or polypropylene glycol (PPG) type suppressor, and a very low concentration of an accelerating compound (e.g., dimercaptopropane sulfonic acid (SPS)). One of ordinary skill in the art would understand that a two component plating bath does not necessarily require two unique "compounds," but may include a single compound or species having a distribution of molecular weights and functionalities. While not wanting to be held to any particular model or theory, functionally the suppressor is a surface-kinetic polarizing compound, and in combination with a surface chemisorbing halide (e.g. chloride or bromide), leads to a substantial (~200-700 mV) increase in voltage drop across the interface. Suppressors are generally (but not always) present at a high "excess" concentration, are generally not consumed in the plating process (i.e., the suppressors are generally not incorporated into the deposit, though they may slowly degrade), and do not exhibit strongly concentration- or flow-dependent behavior around operational flow or concentration levels.

An accelerating compound in most copper damascene and TSV plating baths (most commonly used are Dimercaptopropane Sulfonic Acid, Dimercaptoethane Sulfonic acid, and their derivatives, in TSV bath at a concentration of about 0.5 to 2 ppm) tends to reduce the polarization associated with the presence of the suppressors in the bath, and so "accelerate" the plating rate at locations where it is present relative to regions where it is absent. The combination of the two ingredients is commonly employed. Without going into details (which have been disclosed in detail in prior issued patents including but not limited to U.S. Pat. Nos. 7,449,009, 7,560,016, 7,799,200, and 7,947,163, each incorporated by reference herein in its entirety), the accelerating compound can become strongly adsorbed and generally laterally-surface immobile as a result of the plating reactions. The polarization is thereby reduced as a function of the local surface concentration of the accelerator bound to the plating surface (e.g., the concentration of mercapto-metal bound compound). As a further attribute of the accelerator, except under condition or action of compounds such as a leveler (discussed below) the accelerator may remain surface active and "float" at the surface (i.e., not be incorporated into, buried or converted in the growing film as the metal is deposited on the surface) without further replenishment from the bath. Example accelerators include, but are not limited to, 2-mercaptoethane-sulfonic acid, 3-mercapto-2-propane sulfonic acid, dimercaptopropane sulfonic acid, dimercaptoethane sulfonic acid, 3-mercaptopropionic acid, mercaptopyruvate, 3-mercapto-2-butanol, and 1-thioglycerol.

During bottom up filling, particularly in very large and deep structures such as TSVs, which may take from 10 minutes to several hours to fill, the bottom of the feature becomes depolarized by accumulating a substantially higher surface concentration of the mercapto-metal bound accelerating compound compared to other parts of the plating surface. The relatively higher surface concentration of accelerator and the accompanying depolarization lead to an increased deposition rate at the bottom of the feature. The depolarizing compound may be the same molecule as in the bath, or a breakdown product of that accelerator.

While not wishing to be held to any particular model or theory, it is supposed that the rate of formation of surface adsorbed accelerating compound from the accelerating precursor is a function of voltage, and that the process of adsorption can happen both chemically and electrochemically. At low current/potentials the process is believed to be chemical, and is primarily driven by the free cuprous ion concentration at the plating surface. Conversely, at more negative (higher driving potentials) it is believed that a direct accelerator-electrochemical-reduction mechanism is operative. With increasing reductive current, the chemical rate of formation of surface accelerator bound compound decreases because the reaction is catalyzed by surface adsorbed cuprous ions. The concentration of surface adsorbed catalytic cuprous ions decreases with increasing current and with more negative potentials as the intermediate ion of the two step process ($Cu^{+2}+e-\rightarrow Cu^+$, followed by $Cu^++e-\rightarrow Cu$) is used up at an increasing rate to form copper metal in the plating process. Thus, we suppose that the chemical-driven contribution to the accelerating process decreases with increasing current density. On the other hand, the rate of direct electrochemical reduction and transformation of the SPS or similar accelerator to form the surface adsorbed accelerator species (e.g. a mercaptopropane sulfonic acid or similar derivate) increases with increasing current density and increasingly negative potential. Therefore, it is believed that the rate of formation of accelerating surface species increases as a function of accelerator precursor concentration, but also has a minimum rate of formation at an intermediate current density (e.g., between 0.5 to 2 $mA/cm^2$), and can be impacted by any other factor that modifies the solution and/or surface cuprous ion concentration (e.g. the dissolved oxygen content in the electrolyte).

According to the geometric-area-reduction-driven acceleration model, at the initial stage of the filling process, very little or no accelerator is present at the surface. As time passes and the plating process proceeds and current is supplied, it is believed that the accelerator accumulates at a substantially uniform low concentration over the entire plating surface, including in recesses. However, the otherwise low concentration of accelerator can increase and become concentrated and accumulated at certain locations on a plating surface. For example, the accelerator may become concentrated along an area of a concave/recessed feature (e.g., the bottom of a recessed feature) because as plating occurs and the surface grows, the feature's surface area tends to decrease. This results in an increased surface concentration of the accelerating compound at the feature bottom and a correspondingly increased local plating rate at the feature bottom due to the accelerator's effect of reducing the local kinetic resistance. This allows the feature to fill "bottom-up" due to the relatively lower resistance to plating (its higher "acceleration") at the feature bottom relative to the rest of the surface.

As the feature fills and the accelerator concentration at the moving bottom increases due to the accumulation of accelerator from the material previously at the feature bottom and wall, the current increasingly is directed to the feature bottom and there is a simultaneous reduction of current directed to the other parts of the plating surface, particularly to the side walls of the feature and the field area. This relative current reduction in the field and lower polarization inside the feature causes the potential at all surfaces to drop and the rate of further formation of accelerator on all surfaces to be substantially reduced or stopped. One goal in electroplating is to sustain a differential in accelerator concentration and polarization throughout the entire process. In pursuing this goal, it is therefore useful and sometimes necessary to have the rate of accelerator formation generally decrease and/or stay at a very low rate after the initial period of formation and as metal is plated. However, the rate of accelerator formation does not drop to zero, and so, over the long time associated with TSV filling, there can be a slow but steady concurrent increase in the concentration of accelerating molecules in locations where it is not desirable for achieving optimal fill rate and void free filling (e.g., on the field and upper side wall regions of the feature). If the accelerator compound builds up at these surfaces, it will tend to reduce the surface kinetic resistance at the main field (top) of the feature, and the desired contrast in plating rates between the bottom feature surface and side walls or field may be reduced to cause the filling process to fail. Filling failure may result in the filling stopping and/or the formation of a void in the filled feature. Therefore, careful maintenance of feature filling bath properties over a long time period is beneficial.

One or more leveling compounds present at low concentrations are often beneficial in avoiding feature fill loss. The leveler acts as a suppressing agent which may counteract the tendency of the feature side walls and field to become depolarized as the accelerator compound builds up at these surfaces over time. The use of a leveler is especially beneficial where a chemically active accelerator breakdown product is present because these breakdown products accumulate over time/as multiple wafers are processed, and may be detrimental to the plating process. For example, the buildup of very low levels of chemically adsorbing mercaptopropane sulfonic acid (MPS) in the bath from the precursor dimercaptopropane sulfonic acid (SPS) may cause the field of the wafer to depolarize and lead to feature filling failure, voiding and/or a reduced bath fill rate. Thus, a low concentration of one or more leveling compounds can both aid in the filling process and maintain the filling process uniformity over the processing of many wafers.

In summary, leveling plating compounds (levelers) have the function of reducing the plating rates at regions of the surface which would otherwise be plating at higher plating rates. Classically this would include the edges and exposed portions of a surface. While not wanting to be held to a particular model or theory, levelers are compounds that, by themselves or in combination with other compounds or functional interactions of compounds in a plating bath, serve to increase the polarization (surface resistance) of the electrodeposition reaction locally. Levelers are often present in concentrations that are small (10's of ppms or less). Levelers react or are consumed at the electrode interface at a rate that is at or near a diffusion limited rate. Therefore, a continuous supply of the leveling agent must be maintained, and its distribution at the electrode is greatest at the regions that are most exposed or where convection is greatest. The function of a plating bath leveling compound is generally understood by those skilled in the art to increase, either alone or in combination with other bath additives, the charge transfer (kinetic) interfacial resistance, and it is classically used to suppress growth at a point on a plated surface that would otherwise grow at a rate greater than other locations in the deposit. Though a leveler can operate and be functional by various means depending on the chemical system studied, as specifically applied to many of the embodiments disclosed herein, the function is at least in part to remove the influence of an accelerating compound at the exposed regions of a surface.

Levelers best suited as being measured according to methods described herein have the property (alone or in addition to the above characteristic) of reducing the depolarization of the interface associated with the presence of the accelerator and restoring the underlying suppressed-molecules' polarization (i.e. removing the acceleration, decreasing surface polarization and increasing resistance).

As a specific example, a copper acid plating solution contains sulfuric acid, copper sulfate, a polyethylene oxide/polyethylene glycol suppressor molecule with from 20 to 100 ppm chloride ion (e.g. 50 ppm), and a dimercaptopropane sulfonic acid (SPS) accelerator along with a leveler which tends to deactivate the SPS activity. In accordance with disclosed embodiments, the leveler concentration can be measured. A leveling compound therefore is often a surface kinetically inhibiting molecule and may have the function of being able to remove the depolarizing (accelerating) influence of any accelerator with similar properties (dimercaptopropane sulfonic acid (SPS), mercaptopropane sulfonic acid (MPS), dimercaptoethane sulfonic acid (SES), meraptoethane sulfonic acid (MES), bis-(3-sulfopropyl)-disulfide (DSP), etc.).

Again, while not wishing to be bound by any theory or model, it is believed that, over long periods of time and as charge passes through a plating bath, the concentration and rate of adsorption of certain depolarizing accelerating molecules will locally increase. These molecules directly accumulate on the plated surface via reaction, adsorption, etc., and they include any intermediates, and accelerating reaction products or breakdown products.

Methods of Detecting Leveler Concentration

Methods and associated apparatus of detecting low concentrations of a leveler in a plating bath are described. For convenience, these techniques may be referred to as the Pre-Acceleration-Recovered-Polarization (PARP) methods and apparatus. One detection method is described herein as related to a copper plating bath used for plating through silicon via structures (TSVs), but the concept is not so limited in application or metal (other applications and plating materials include, e.g., Damascene, bump, pad and connector tab plating, and the metal of tin, silver, nickel, gold, etc.). An electrochemical plating apparatus suitable for maintaining a reproducible mass transfer convected flow to the working electrode is typically used. It may provide a controlled temperature and mass transfer boundary layer. An example of such plating apparatus is one including a rotating ring/disk/cylinder electrode, or an impinging jet or fountain, and a moving paddle (paddle plater).

In some embodiments, the first step of the PARD measuring process is preparing a metal-plated electrode such as a copper plated electrode. This process is sometimes referred to as the pre-analysis plating step or the pre-plating step. One function of this step is to create a clean metal surface used in the later analysis, where the surface is made of the same metal contained in the plating bath which is to be analyzed. If the initial rotating disk electrode (RDE) is an inert electrode (e.g. an electrode made or coated with platinum) and the solution to be analyzed is a copper plating solution, then the first step may involve plating the inert RDE with copper. The plating can occur in, for example, a copper plating solution, which may be the same or different than the plating solution to be measured (i.e. the plating solution used in this step may contain different chemical concentrations of physically the same entities as those found in the plating solution to be tested). In a simple case, the plating solution contains a cupric salt and an acid (e.g., copper sulfate and sulfuric acid). In some embodiments, the pre-plating solution does not contain appreciable quantities organic plating additives. In some cases, the pre-plating operation may include one or more additives (e.g., suppressor, an accelerator, and optionally a leveler) so as to produce a smooth and bright surface.

Generally the plated surface created should either already contain, and/or be receptive to, a strongly adsorbing accelerating compound (such as mercaptopropane sulfonic acid in the case a typical of copper plating bath). Therefore, the plated surface should not contain any materials which would interfere with the adsorption of the accelerating compound. A plating solution used in the pre-analysis plating step may be free of additives, containing only copper salts and optionally an acid in an aqueous solution (e.g., 60 g/L copper ion and 60 g/L sulfuric acid). However, depending on the initial underlying substrate quality and the thickness of the pre-analysis plating, the microroughness of the surface produced may be less than optimal. Therefore, in some embodiments the pre-analysis plating is performed in a bath with characteristics/additives that lead to a smooth, bright deposit. Adding one or more suppressor agents to the pre-analysis plating solution may slightly improve this roughness factor. One type of pre-analysis plating solution that can lead to a smooth, bright deposit that does not have accelerator-adsorbing interfering molecules present after the plating process, is a solution containing both suppressing and accelerating additives. For example, the pre-analysis plating can be performed in a solution containing 60 g/L copper ion, 60 g/L sulfuric acid, 5 ppm SPS, and 100 ppm of a PEO compound from BASF known as L62. The current density used may range from about 1 to 50 mA/cm$^2$ and can be applied from about 1 to 100 seconds at a temperature of between about 10° C. and 35° C.

A typical TSV plating solution that would benefit from having its low concentration of leveler measured and monitored is one that contains copper sulfate or copper methane sulphonate at a concentration of about 20 to 100 g/L, sulfuric acid or methane sulfonic acid at concentrations of about 20 to 100 g/L, and has a total dissolved solid concentration between about 1.0 to 1.8 M/L (acid plus metal salts) and below the solubility limit for copper ions. Such plating solutions typically contain chloride ions at a concentration ranging from about 10 to 100 ppm, more commonly between 25 and 75 ppm. The plating solution will also generally contain an accelerating compound such as SPS (dimercaptopropane sulfonic acid) at a concentration between about 0.2 and 2 ppm, or as an alternative, the Moses Lake Industries proprietary accelerator "HSL-A" in a concentration between about 0.1 to 2 ml/L. Further, the TSV bath typically contains a suppressing agent, for example, a PEO-based suppressing compound such as L62 from BASF at a concentration between about 50 to 400 ppm. As an alternative, the suppressing agent may be a proprietary suppressor called "HSL-B" from Moses Lake Industries, at a concentration between about 0.5 to 1 ml/L. A plating bath benefitting from leveler concentration measurement may also contain Janus Green B at a concentration between about 0.05 to 2 ppm, or the Moses Lake Industries proprietary leveling compound "HSL-C" at a concentration between about 0.05 and 2 ml/L. This concentration range for HSL-C is believed to correspond to an active leveling molecular concentration below about 2 ppm. The HSL-C leveling compound is used as an example of a measured low concentration leveling compound in a TSV plating solution in later examples, though one of skill in the art would understand that the methods and apparatus disclosed are not so limited. Many other compositions may be used. Generally, the compositions contain a leveler and an accelerator.

In some cases, plating bath vendors may blend and combine the functionality of the leveler agent with other agents (suppressors or accelerators, grain refiners, wetting agents, etc.), as a constituent of an "additive." In other cases, the vendor may not know of the functional presence of a leveler compound in their additive, for example because it is at particularly low levels and may be a byproduct or residual of the production process of the target additive itself. As an example of this possibility, manufactured blends of a molecular weight distribution of a polymer acting as a suppressor are common, and such blends may have a range of both functionalities and responses. They may further include low levels of the low molecular weight (e.g. monomer) moiety or very high molecular weight fragments that can have the general operative properties of a leveler. Thus, the presence of the relevant target leveler compound or group of compounds may only be distinguishable with careful analysis and study, including but not limited to comparative study of a standard vs. a measured electrochemical response of the bath using the procedure and apparatuses described herein, and not by the vendors technical data sheets, proclamation, or nomenclature.

In some embodiments, an objective of the pre-analysis plating step is to create a microscopically reproducible copper plated surface onto the foreign substrate (Pt) for subsequent processes and measurements. The deposited copper or other layer should continuously coat the entire electrode surface. The deposited layer does not need to be very thick (e.g. less than about 2 micrometers). Thinner layers may be preferable because after measurements are made in subsequent operations, a thicker film would require more time and effort to recover and expose the noble metal substrate. The thickness is sometimes on the order of the thickness of a conventional copper seed layer used in plating a wafer (e.g., between about 500 to 2,000 Å). In alternative embodiments, the copper layer is provided by electroless deposition, or by a non-electrochemical deposition technique such as PVD. The copper layer may also be provided as a solid piece of pure copper disk or rod that is etched and cleaned prior to the accelerating pre-treatment.

After performing the pre-analysis plating with the pre-analysis plating solution, the electrode is removed from the solution and optionally rinsed with, e.g., deionized (DI) water. Alternatively, the solution is drained from the pre-analysis plating cell and rinse water is added while the disk remains stationary. The next step in the PARP process, the pre-acceleration step, typically produces a surface-adsorbed and substantially saturated accelerator at the prepared copper surface. This result is achieved by exposing the surface to a solution of concentrated accelerating compound or compounds, sometimes referred to as a pre-acceleration solution, for a sufficient time to achieve substantial saturation. This accelerator-adsorption operation is further discussed in the patents incorporated by reference above. An example of the pre-acceleration step is the exposure of the plated copper surface for 10 seconds in a solution containing 1 g/L mercaptopropane sulfonic acid (this is the monomer of dimercaptopropoane sulfonic acid and is highly chemically reactive with the copper surface).

The exact time of contact, the accelerating compound(s) used and their concentrations, should be sufficient to achieve a saturation state. At this saturation state, higher accelerator doses (higher concentrations and/or exposure times) will generally result in no measureable change in the electrochemical properties of the surface. Operating under saturation conditions creates a uniform and reproducible starting state from which the interaction of the leveler with the surface can be both detected and measured. While it is possible to analyze the system at a state below saturation, it tends to require a higher degree of dosing exposure control, with the influence on the degree of acceleration being a function several variables including the concentration of accelerator(s) in solution, the time of the exposure, the temperature, and the convection at the electrode's surface. Therefore, while not required, it is preferable to achieve a saturated state when practicing the PARD process.

With the surface fully accelerated, the electrode can easily and readily yield a reproducibly deterministic interaction with leveler in solution. Examples of accelerators that may be used to produce the saturated electrode surface include SPS, MPS, SES, MES, and DSP. In some embodiments, the pre-plating and pre-acceleration steps can be combined by using a pre-plating solution having an appropriate amount of one or more accelerators in the pre-plating solution, and using a sufficiently long exposure time and/or applied current in the pre-plating operation to achieve a substantially accelerator-saturated pre-plated surface.

After producing a saturated electrode surface, the accelerating solution is drained or otherwise removed from contact with the electrode surface, and the electrode is typically spun to remove entrained solution, followed by completely rinsing the electrode with water. An extensive cleaning and rinsing process is beneficial in order to avoid transferring any excess accelerating compound left in the container/cell or on the electrode surface to the test plating solution that is about to be measured. The only accelerator in the test cell may be accelerator adsorbed onto the electrode surface.

Next the interaction between the accelerator-saturated surface and the leveler in solution is detected and characterized through the polarization recovery portion of the PARP process. In some embodiments, after rinsing, the copper or other metal pre-plated and pre-accelerated electrode undergoes electrodeposition in the solution containing the leveler to be measured (either to produce a standard response for calibration purposes, or to measure the leveler in a solution with an unknown concentration of the leveler). As the leveler is present at relatively low concentrations, operating at extremely high convective conditions may be beneficial in detecting and measuring a sizeable signal because the high convective conditions result in an increased rate of flux of leveler to the surface and a shorter polarization recovery and measurement time. These conditions enhance the rate of interaction and amplify the leveler signal which can be measured on a small measuring electrode such as an RDE. Therefore, the convective conditions are typically much more aggressive than those applied in the TSV plating process, because, at least in part, during TSV plating it is undesirable for leveler to be transported deep into the bottom or deep into the side walls of the TSV structure. The leveler action during TSV plating needs to be confined to the upper regions of the structure and the field.

As an example, the rotation rate of the RDE (e.g. an RDE having a surface area of about $0.125$ $cm^2$) in this portion of the analysis is greater than about 400 rpm or greater than about 800 rpm or greater than about 1000 rpm, for example 1600 rpm. This 1600 rpm rotation rate reduces the boundary layer thickness as compared to an RDE operated at 100 rpm by a factor of about 4, and an RDE operated at 25 rpm (typically used in a TSV plating application) by a factor of about 8. According to the Levich equation, the flux of a diffusion control element to a surface of a rotating disk increases with the square root of rotation rate. The mass transfer boundary layer thickness for a molecule such as a copper ion in water with a diffusion coefficient of about $5E-6$ $cm^2/sec$ at these rotation rates is quite small, specifically about 40 micrometers at 100 rpm, 20 micrometers at 400 rpm, and 10 micrometers at 1600 rpm The uniformly high convective conditions serve to speed up the rate at which the leveler can repolarize the pre-accelerated surface. The volume of solution used in this operation should be relatively small relative to the size of the plating bath (e.g., less than 100 mL, less than 50 mL or less than 25 mL). Although larger volumes of solution may be used, it is beneficial to use smaller volumes to reduce the cost of waste solution and to conserve solution, as well as to reduce capital expenditure (sizing of pumps, valves, cells, etc.) and therefore to save cost.

By measuring the electrochemical response (e.g., voltammetric/polaragraphic responses) and characterizing it against a set of standards or a model, the concentration in the unknown bath can be determined. In various embodiments, the model relates leveler concentration as a dependent variable to electrochemical response of the test sample as an independent variable. Various techniques may be employed to derive leveler concentration in the test sample from the electrochemical response. In some cases, the relation is performed automatically. For example, the model may take the form of an equation or other mathematical relationship relating leveler concentration to electrochemical response. Other approaches may involve interpolating between or extrapolating from leveler concentration values associated with previously recorded electrochemical responses.

The electrochemical response (as an independent variable) may be properly measured and characterized by various techniques. Two basic illustrative methods for measuring the electrochemical response include (1) plating at a constant current and monitoring the potential at the electrode, and (2) plating at a constant potential and monitoring the current supplied to the electrode or the current density at the electrode or in solution. Other methods may include sweeping of potential or voltage, pulsing of there variables, modifying the rotation rate, etc. Combinations of these techniques may also be used. As a specific example, a constant current plating at between about 0.5 and 40 $mA/cm^2$ may be employed at 1600 rpm, and the time to reach a particular target reduction voltage increase compared to the initial open circuit potential (i.e., the time it takes for the potential to become a degree more negative or become a degree more reductively polarized) can be correlated with leveler concentration to predict an unknown bath composition. Alternatively, constant potential plating at a polarization of between about 100 to 700 mV vs. the open circuit potential can be applied and the time for the current density to fall to a particular value or the total charge passed to reach a particular value can be correlated with leveler bath composition. See the discussion of FIGS. 2-4 below for a further explanation of certain exemplary techniques. Again, many forms of voltammetry (sweeping, stripping, AC impedance, etc.) can be used to characterize and compare the electrochemical response of the accelerator-saturated test electrode. The voltammetry methods generally do not modify the underlying process or principles of the PARP processes, including recovering the polarization by the leveler on a surface which is purposely pre-saturated with an accelerating compound.

After the interaction between the leveler and the accelerator-saturated electrode is complete, the electrode may be treated to regenerate it to its starting condition. For example, in many implementations, some or all of the copper or other metal plated onto the electrode during the test solution analysis and pre-plating operations is removed. The removal may be accomplished by any suitable technique including mechanical, chemical, and electrochemical techniques. In one example, the metal layer is removed by chemical etching such as etching with an acidic oxidizing solution. A specific example of a suitable copper etching solution is a mixture of 5%/wt hydrogen peroxide with 5%/wt sulfuric acid. In the case of copper, one suitable chemical etching solution contains peroxide and acid. Alternatively, the electrode metal may be removed electrochemically, e.g., by voltametric anodization. In one implementation, the electrode metal is removed by reversing the polarization after the analysis portion of the test while the electrode is still in the test solution, before the test solution is disposed of. Chemical mechanical polishing and electropolishing of the surface may also be used.

In certain embodiments, the metal pre-plating is done in the test solution, and after pre-acceleration of the surface and rinsing the electrode surface, the electrode is immersed again in the test solution where voltammetry is performed by potentiostatic or galvanostatic plating, or galvanometric or potentiometric sweeping followed by stripping. In other embodiments, a first solution with a known concentration of leveler is provided, and a second solution with an unknown concentration of leveler is "dosed" into the first solution to form a third solution. The third solution is then tested according to the methods described herein (e.g., an electrode with a metal surface is provided and saturated in a pre-acceleration solution, then rinsed, then plated in the third solution as an electrochemical response of the electrode is measured, and then the electrochemical response is used to determine the concentration of leveler in the third solution). At this point, the unknown concentration of leveler in the second solution can be calculated based on the known concentration in the first solution, the determined concentration in the third solution, and the amount of the second solution that was added to form the third solution.

In certain embodiments, the complete sequence from pre-plating to measuring the electrochemical interaction between the leveler and accelerator-saturated electrode is repeated for each measurement. The frequency of the measurements will vary depending on various factors. In a typical continuous flow semiconductor wafer plating apparatus, it may be appropriate to test the leveler concentration 1 to 10 times per day (or after a defined amount of charge is passed through the electrolyte or a defined number of wafers are plated). Note that the plating solution is routinely tested for the concentrations of other components such as copper salt, acid, accelerator, and suppressor. The leveler measurement may be made at the same time as these other measurements or at a different time. The measuring tool may need to be recalibrated using known leveler concentrations. Recalibration may be appropriate every measurement, every few days or over a period of weeks, depending on the desired accuracy.

It should be understood that the leveler measurement may be employed as part of a dosing system on the tool. Further, the measurement result (e.g., the calculated concentration information) may drive a corrective dosing process for maintaining the bath concentration of the low leveler concentration, or simply an operator notification or tool such as an "out of control" issue alarm. For example, the measurement may be made as a pass vs. no pass condition with either no action or a trigger for a set of out-of-specification-range operations, including but not limited to auditory, visual, tool driven shutdown or other condition-driven responses. More commonly, once the concentration of leveler in solution is characterized, this information can be used to adjust the concentration of leveler in solution as appropriate to maintain a relatively constant leveler concentration over time. These adjustments may occur by adding doses of additional leveler as desired, either manually, automatically or semi-automatically.

Figure 1:
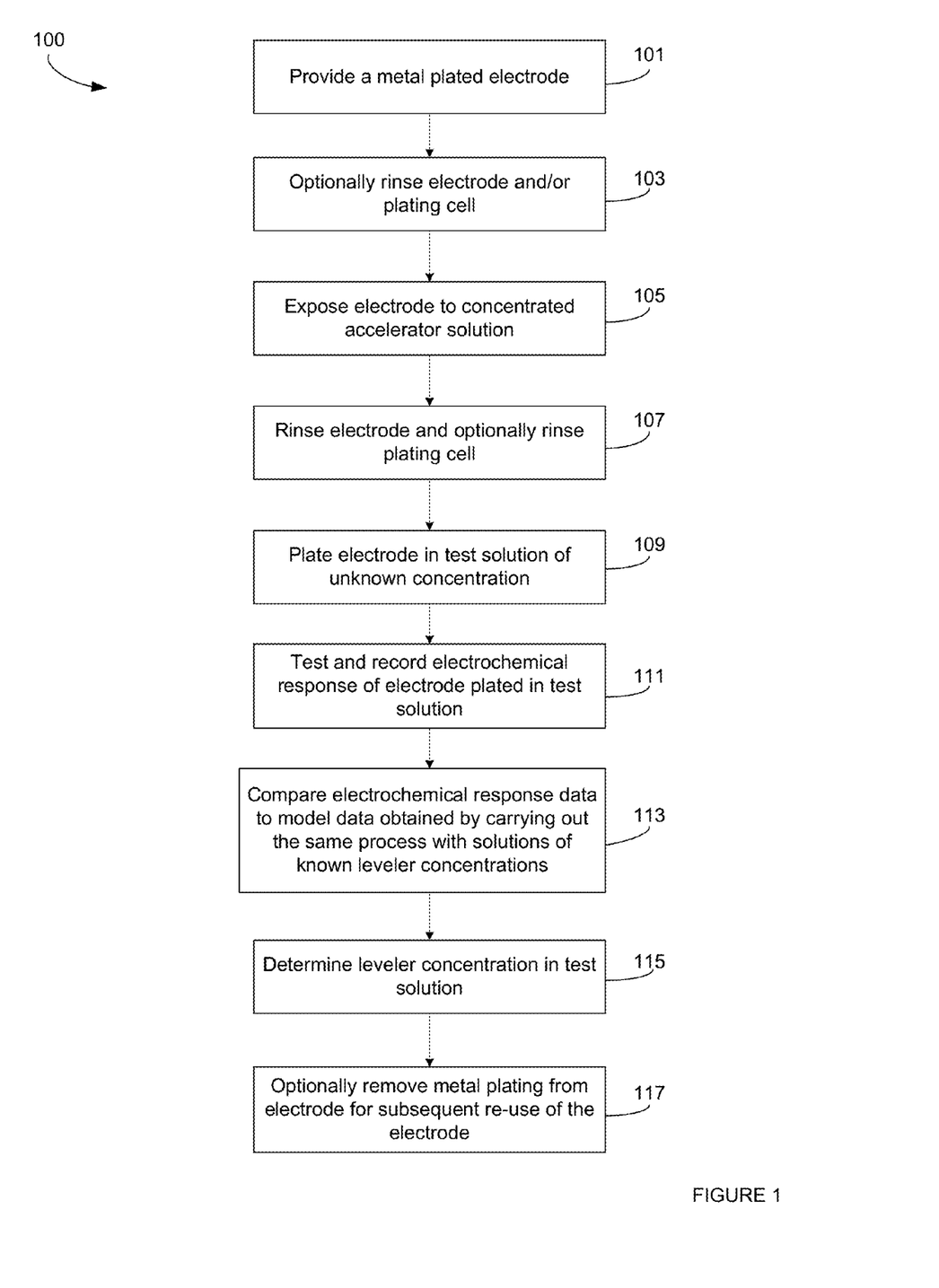
FIG. 1 is flow diagram illustrating an example process for determining the concentration of leveler in a solution.

One implementation of the method of determining the concentration of leveler in solution is depicted in FIG. 1. Process 100 begins at block 101 where a metal plated electrode is provided. This operation may include pre-plating an electrode with copper or another metal. Alternatively, the electrode as provided may already be plated with metal, or the electrode may be substantially made of copper or other metal, in which case pre-plating is not needed, although the surface of such electrode may be etched or otherwise treated to provide a consistent surface quality prior to each measurement. At block 103 the electrode and plating cell are optionally rinsed. At block 105 the electrode is exposed to a concentrated accelerator solution, sometimes referred to as a pre-accelerator solution. As described above, the electrode should be allowed to become saturated with accelerator during this operation. At block 107 the electrode and plating cell are optionally rinsed. This removes any unadsorbed accelerator and prevents it from transferring into the test solution. At block 109 the electrode is plated in the test solution with unknown leveler concentration. In many embodiments, this operation is performed at high convective conditions relative to those typically used during TSV plating.

Figure 2:
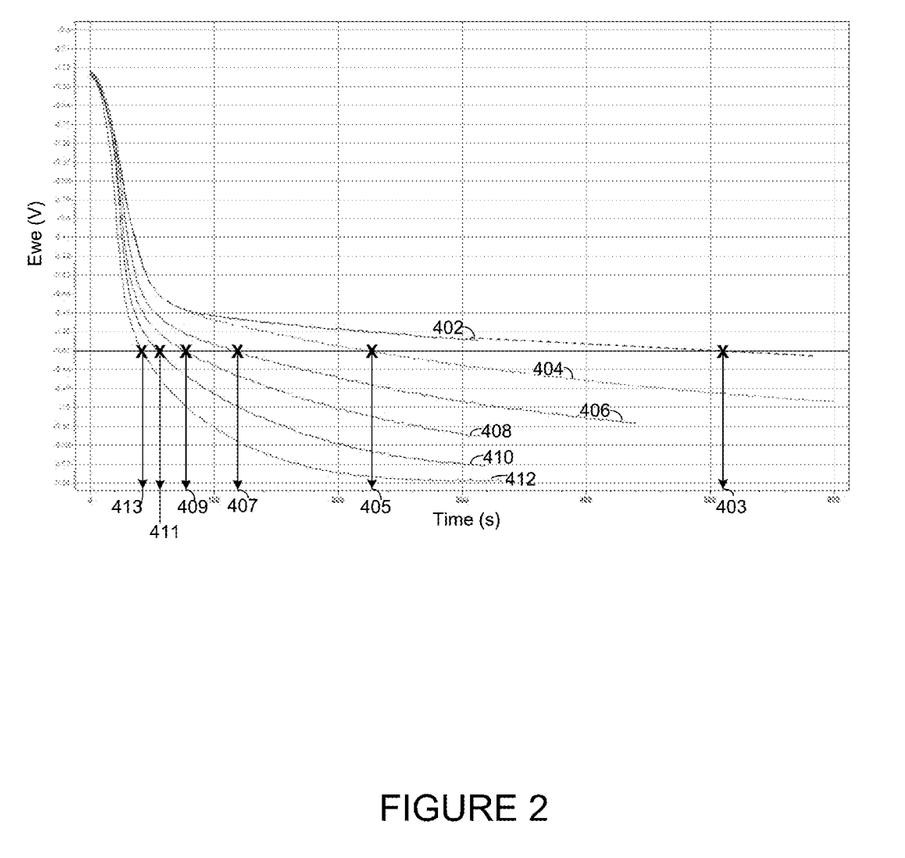
FIG. 2 is a graph of $E_{we}$ (V) vs. time (s) after a step change in applied current density from 0 to 8 mA/cm$^2$ at 1600 RPM for different solutions of known leveler concentrations.

After the electrode is plated in the test solution, the electrochemical response of the electrode is tested and recorded in block 111. The electrochemical response may be tested in various ways, as described herein. At block 113, the electrochemical response obtained in block 111 is compared to model data. The model data may be generated by performing the same operations (101, 103, 105, 107, 109\*, 111 and 117) described in FIG. 1, using solutions of known concentrations in block 109\* instead of the test solution of unknown concentration. With this method, it is possible to generate sets of model electrochemical response data against which the electrochemical response of the electrode plated in the test solution can be compared. Next, the concentration of leveler in the test solution is determined in block 115. This determination is driven by the comparative data generated/used in blocks 111 and 113. In block 117 the metal plating is optionally removed from the electrode. Removal of the metal plating allows the electrode to be reused in a subsequent analysis. One set of model/calibration data is shown in FIG. 2. Each plotted line represents the electrochemical response $E_{we}$ (V) after a step change in applied current density from 0 to 8 mA/cm² at 1600 RPM. $E_{we}$ is the voltage "V" of the working electrode as a function of time vs. a reference electrode, in this case the reference electrode is a Hg/HgSO$_4$ reference electrode of a calibration solution with a known amount of accelerator, suppressor and leveler. In this example, each calibration solution is prepared with 1 mL/L accelerator HSL-A and 5 mL/L of HSL-B suppressor. The response at various concentrations of leveler HSL-C in the solutions are represented by curves 402, 404, 406, 408, 410 and 412, with corresponding leveler concentrations of 0.0, 0.125, 0.25, 0.5, 1.0 and 2.0 ml/L, respectively.

A polarization change target point is selected at a certain value, in this case at −0.47 V. The polarization change point is somewhat arbitrary, but should be selected based on the range of leveler concentration typically present in solution, as well as the sensitivity of the data. Times 403, 405, 407, 409, 411 and 413 represent the time that it took each corresponding solution to reach the chosen polarization change point. The figure shows that solutions with higher concentrations of leveler reach the polarization change point faster than solutions with lower concentrations of leveler. Note that to avoid a loss of accuracy associated with a drift in the potential of the reference electrode over time, one can normalize the potential by using a potential change relative to the initial open circuit potential. In this case, the initial open circuit potential for each case is about −0.324 V vs. Hg/Hg/SO$_4$. If the reference potential shifts, it becomes evident in the shift of the initial open circuit potential just before or very shortly after the application of the current during the test. Thus, by tracking the potential difference relative to the potential just prior to or very shortly after the start of the current step, one can in principle avoid inaccuracies associated with minor reference potential electrode drift.

Figure 3:
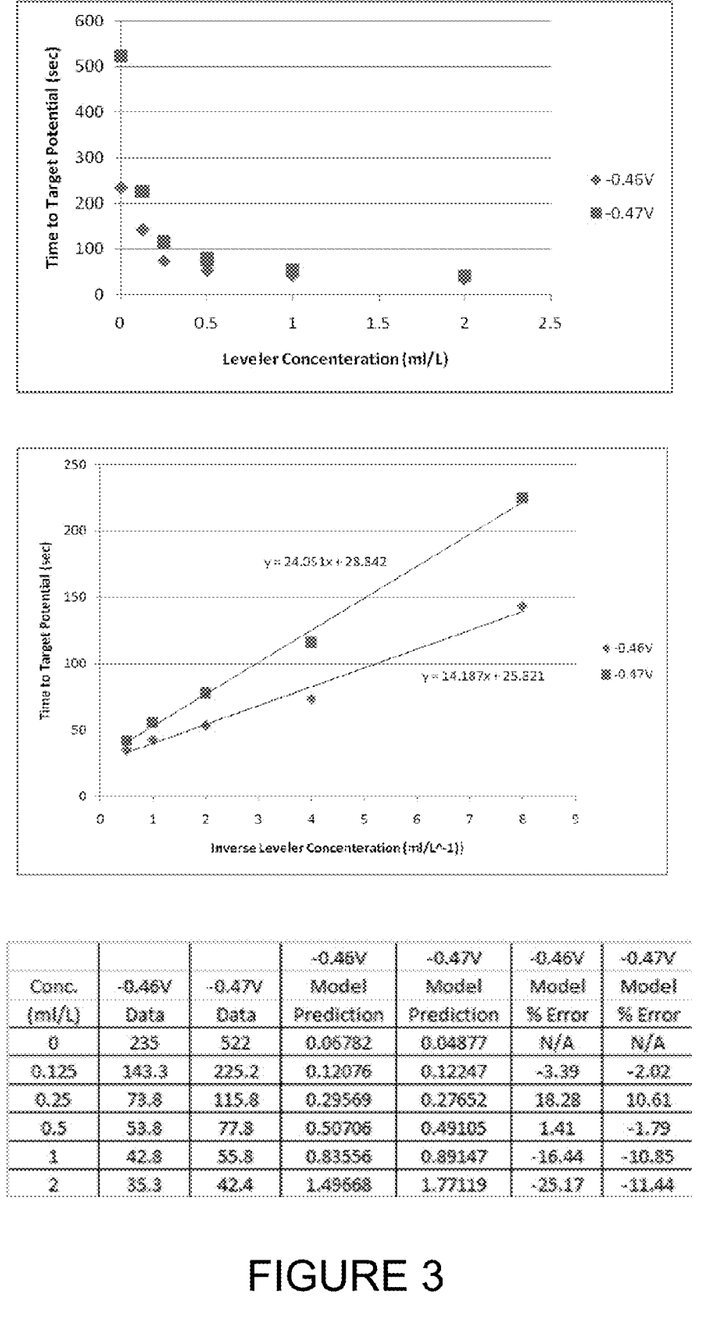
FIG. 3 contains three panels. The upper panel of FIG. 3 shows the time it took for each solution in FIG. 2 to reach a target potential vs. the concentration of leveler in solution. The middle panel of FIG. 3 shows the time it took for each solution in FIG. 2 to reach a target potential vs. the inverse of the leveler concentration, and two models generated by fitting the data to a linear model. The bottom panel of FIG. 3 shows a table corresponding to the data and models in the middle panel of FIG. 3.

FIG. 3 shows a further method of presenting comparative calibration data. The data in this figure correspond to the data shown in FIG. 2. In the upper panel in FIG. 3, the time to reach a target potential (the polarization change point) is plotted against the leveler concentration. In the middle panel in FIG. 3, the time to reach a target potential (the polarization change point) is plotted against the inverse of the leveler concentration. In each case, two sets of data are plotted. One data set relates to a polarization change point selected at −0.47 V, while the second data set relates to a polarization change point selected at −0.46 V. The middle panel of FIG. 3 further includes a numerical model prediction corresponding to a best linear fit between the time to the target potential and the inverse concentration of leveler. The table in the lower panel of FIG. 3 corresponds to the numerical model shown in the middle panel of FIG. 3, with the model prediction of the concentration based on a linear best fit relationship of time vs. inverse concentration used to calculate the "modeled" concentration. Those modeled calculation are then compared in the last two column for the two cases (time to reach −0.46 vs. or time to reach −0.47V) to determine a model error (zero error would mean that at that point, the model calculated concentration and the actual concentration of the solution as constructed were identical). The results show a reasonably good correlation.

Figure 4:
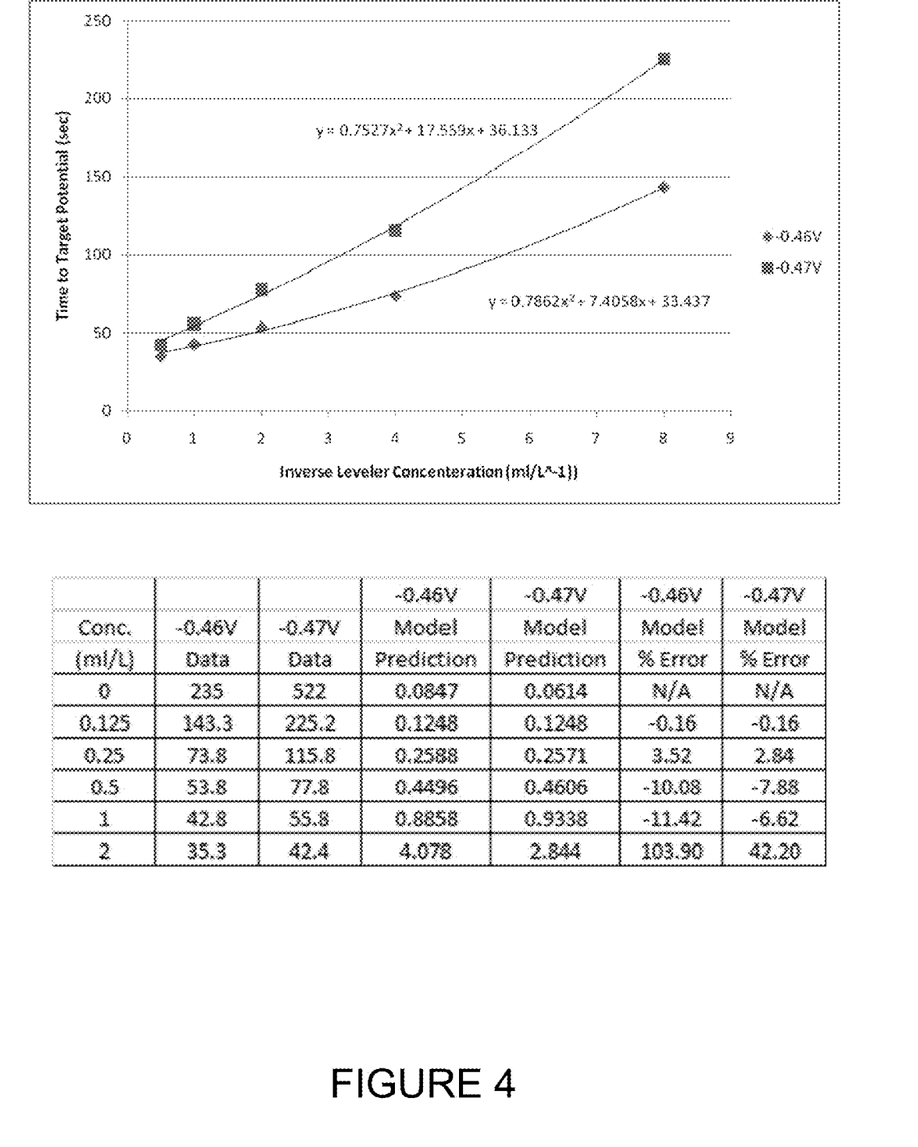
FIG. 4 contains two panels. The upper panel of FIG. 4 shows the time it took for each solution in FIG. 2 to reach a target potential vs. the inverse of the leveler concentration, and two models generated by fitting the data to a quadratic model. The bottom panel of FIG. 4 shows a table corresponding to the data and models in the top panel of FIG. 4.

FIG. 4 shows an additional method of presenting comparative calibration data which in this case leads to a reduction in the degree of error between the predicted and target sample (concentration of the calibration solutions) relative to the method of FIG. 3 (which was a more simple linear correlation of time to inverse concentration). In the upper panel of FIG. 4, the time to reach a target potential (the polarization change point) is plotted against the inverse of the leveler concentration, as in FIG. 3. The numerical model in FIG. 4, however, corresponds to a quadratic fit model, as opposed to the linear fit model shown in FIG. 3. The table in the lower panel of FIG. 4 corresponds to the model shown in the upper panel of FIG. 4. FIGS. 3 and 4 are illustrative of different models which could be used to determine the concentration of leveler in a solution, as the models may be used to compare calibration data against specific electrochemical results obtained from an electrode plated in the solution of unknown leveler concentration. One of ordinary skill in the art would recognize that different types of electrochemical responses may be tested and analyzed, and that many different types of models may be used to characterize the leveler concentration.

Testing and Plating Apparatus

In various embodiments, the leveler concentration is measured ex situ (i.e., outside of the tool and bath used for plating). In such embodiments, the bath sample is extracted from the bath tank, processed on a separate testing apparatus, and the concentration is measured outside the main plating apparatus. Nevertheless, the goal is typically to measure the leveler concentration as it currently exists in the bath (or very recently existed) in the plating apparatus or in the reservoir providing plating solution to a plating cell where the workpiece is processed. To this end, a test sample of the plating solution may be extracted from the reservoir or other component of the fluidic system of a plating apparatus.

In one embodiment where the analytical equipment is separate from the workpiece plating tool, a flow loop is provided and electrolyte continuously recirculates from the plating bath/apparatus to the analytical tool and back to the plating bath. In such an embodiment, when a sample of electrolyte is required for analysis, the sample may be drawn directly from the circulation loop. In some implementations, the analysis tool is associated with multiple plating baths. This implementation further includes appropriate switching valves which allow a single analysis tool to easily and effectively monitor multiple plating baths. The sample is placed in an analytical test cell containing the accelerator-saturated electrode as described above, and the sample is then tested for leveler concentration as described. In other embodiments, leveler concentration is measured in situ (i.e., inside a bath on the tool itself, after preparing a pre-accelerated electrode as described above as part of the PARP process. The apparatus described herein may be deployed proximate the plating bath reservoir used to supply one or more plating cells actively plating wafers or other work pieces.

The test procedure may be conducted manually, automatically, or semi-automatically. In one example of a fully automatic procedure, the electrode and an associated fluid-containing vessel are automatically brought in contact with a series of fluids. For example, the vessel may initially be filled with a solution for pre-plating the electrode with, e.g., copper. The electrode is then immersed in the pre-plating solution and plated (alternatively, the electrode may become immersed as the fluid level rises in the container while the electrode remains vertically fixed in space). Thereafter, the electrode and/or plating solution are removed from the vessel and a rinse solution is introduced. The electrode is then immersed into the vessel and rotated or otherwise agitated to rinse the surface. Then the rinse solution and/or the electrode are removed and the accelerator solution is introduced to the vessel (as above, the electrode may stay vertically stationary and fluid may fill the container to a level where the electrode surface becomes immersed). As explained, the accelerator should be present in sufficient concentration so that the electrode surface becomes saturated with accelerator in a relatively short period of time. When the accelerator solution is present in the vessel, the electrode is immersed and optionally rotated to saturate the electrode surface (e.g., the freshly deposited copper surface). Next, the electrode is rinsed. This may be accomplished by replacing the accelerator solution with deionized water and then immersing the electrode. It should be understood that any step where the electrode is rinsed can be accomplished by spraying the electrode while it is positioned outside the vessel. After the electrode surface is saturated with accelerator and rinsed, the test solution is introduced into the vessel whereupon the electrode is introduced into the solution and subjected to an electrochemical activation (e.g., galvanostatic plating). The electrochemical response is then measured (e.g., voltage transients) and the leveler concentration is characterized. The characterization may be accomplished through the use of a controller such as a microprocessor that is programmed with instructions.

In another approach to testing, any two or more of the solutions used in the pre-plating, rinsing, accelerator coating, rinsing, and electrochemically probing the test solution may be provided in different vessels. These vessels may be provided on a conveyance mechanism such as a belt or platen/wheel to move them into and out of position with the electrode. Alternatively, the vessels may be stationary and the electrode may move as needed.

Any of the vessels in the above embodiments may be filled manually or automatically.

In general, suitable apparatus include hardware for accomplishing the process operations and a system controller having instructions for controlling process operations in accordance with the disclosed implementations. The controller may act on various inputs including user inputs or sensed inputs from, e.g., potential or current readings from a rotating disk electrode in the plating bath reservoir or in an ex situ metrology tool. In response to pertinent inputs, the controller executes control instructions for causing the apparatus to operate in a particular manner. For example, the controller may cause the dispensing of various fluids into the vessel(s). It may also cause delivery of a defined current and/or potential during measurement of the test sample. It may also receive signals from sensors such as signals indicating current transients, voltage transients, coulombs passed, etc. from the electrode in the test sample. Further, if the controller is associated with the main plating system, it may instruct the additive dosing system and/or the bleed and feed mechanisms to adjust the level of leveler delivery or other controllable feature of the apparatus to adjust or maintain the concentration of leveler at a particular defined numerical range in the reservoir and at a different defined numerical range within the electroplating cell. In this regard the controller may be configured, for example, to operate an additive delivery mechanism in a manner that maintains the leveler concentration at about 0.1 ppm to 100 ppm in the reservoir (or at some other point downstream from the electroplating cell in the recirculation loop). The system controller will typically include one or more memory devices and one or more processors configured to execute the instructions so that the apparatus will perform a method in accordance with the disclosed implementations. Machine-readable media containing instructions for controlling process operations in accordance with the disclosed implementations may be coupled to the system controller.

Figure 5:
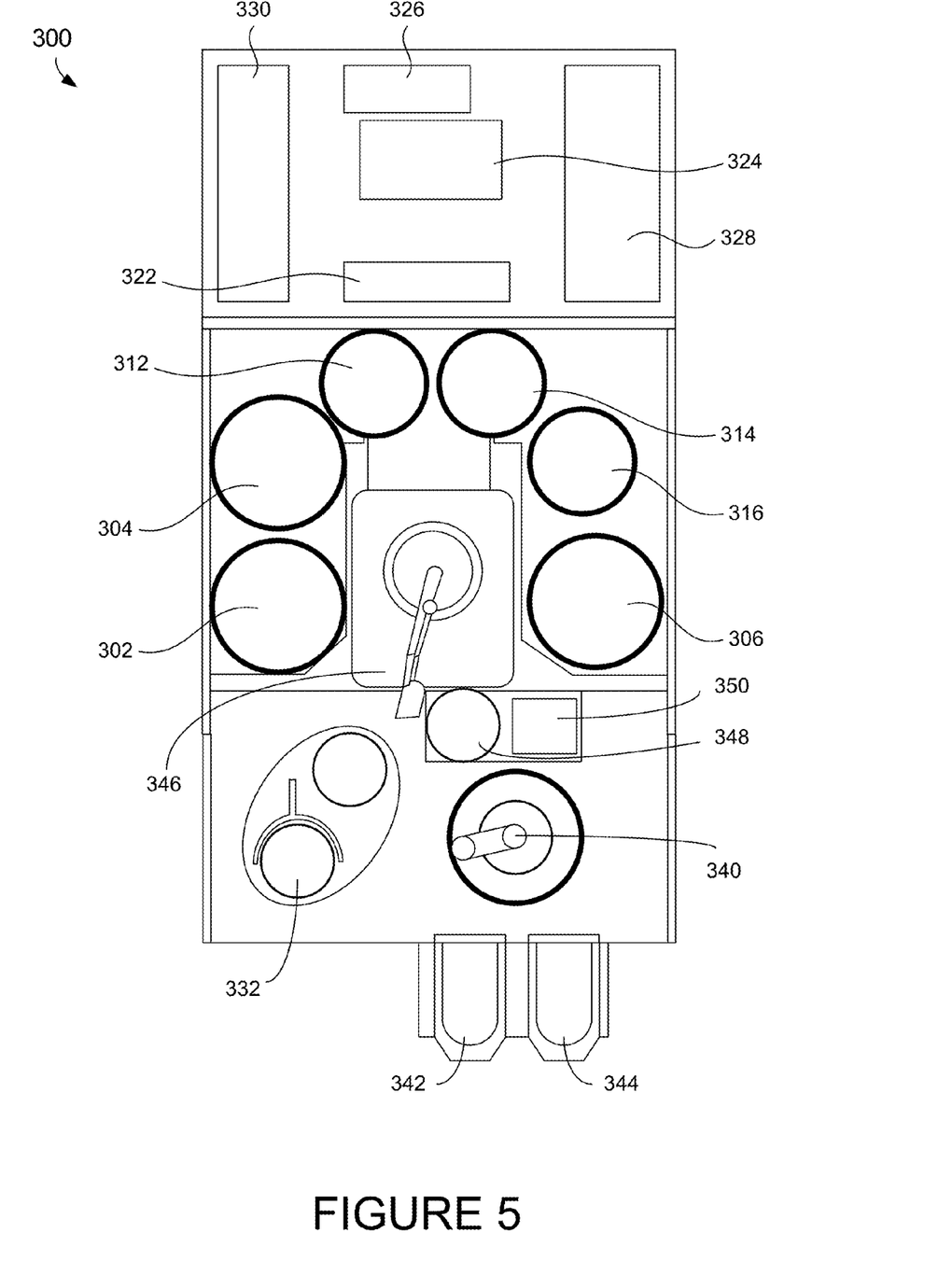
FIG. 5 is a schematic depiction of an electroplating system having multiple plating cells.

FIG. 5 shows a schematic illustration of an example electrofill system 300. The electrofill system 300 includes three separate electrofill modules 302, 304, and 306. The electrofill system 300 also includes three separate post electrofill modules (PEMs) 312, 314, and 316 configured for various process operations. The modules 312, 314, and 316 may be post electrofill modules (PEMs), each configured to perform a function such as edge bevel removal, backside etching, front size metal etching, and acid cleaning of wafers after they have been processed by one of the electrofill modules 302, 304, and 306.

The electrofill system 300 includes a central electrofill chamber 324. The central electrofill chamber 324 is a chamber that holds the chemical solution used as the plating solution in the electrofill modules. The electrofill system 300 also includes a dosing system 326 that may store and deliver chemical additives for the plating solution. A chemical dilution module 322 may store and mix chemicals to be used as an etchant, for example, in a PEM. A filtration and pumping unit 328 may filter the plating solution for the central electrofill chamber 324 and pump it to the electrofill modules. The system optionally includes a degassing device or degassing devices and a reservoir or reservoirs (not shown), as described above. The plating solution may pass through the degassing device before it is pumped to the electroplating modules. The plating solution may pass through the reservoir after it flows out of the electroplating modules.

A system controller 330 provides the electronic and interface controls to operate the electrofill system 300. The system controller 330 generally includes one or more memory devices and one or more processors configured to execute instructions so that the apparatus can perform a method in accordance with the implementations described herein. Machine-readable media containing instructions for controlling process operations in accordance with the implementations described herein may be coupled to the system controller. The system controller 330 may also include a power supply for the electrofill system 300. As mentioned above, in one embodiment, leveler metrology is performed by a piece of equipment physically separated from the plating tool, but fluidically in communication with the plating bath by a flow loop allowing for bath samples to be extracted. In other embodiments, the leveler metrology equipment would still employ means for extracting bath samples, but the equipment will be within the shell of the plating apparatus itself, for example, between the chemical dilution module 322 and the central electrofill chamber 324 or in the filter and pumping unit 328 of FIG. 5.

An example of an electroplating module and associated components is shown in U.S. patent application Ser. No. 12/786,329, entitled "PULSE SEQUENCE FOR PLATING ON THIN SEED LAYERS," filed May 24, 2010, which is herein incorporated by reference.

In operation, a hand-off tool 340 may select a wafer from a wafer cassette such as the cassette 342 or the cassette 344. The cassettes 342 or 344 may be front opening unified pods (FOUPs). A FOUP is an enclosure designed to hold wafers securely and safely in a controlled environment and to allow the wafers to be removed for processing or measurement by tools equipped with appropriate load ports and robotic handling systems. The hand-off tool 340 may hold the wafer using a vacuum attachment or some other attaching mechanism.

The hand-off tool 340 may interface with an annealing station 332, the cassettes 342 or 344, a transfer station 350, or an aligner 348. From the transfer station 350, a hand-off tool 346 may gain access to the wafer. The transfer station 350 may be a slot or a position from and to which hand-off tools 340 and 346 may pass wafers without going through the aligner 348. In some implementations, however, to ensure that a wafer is properly aligned on the hand-off tool 346 for precision delivery to an electrofill module, the hand-off tool 346 may align the wafer with an aligner 348. The hand-off tool 346 may also deliver a wafer to one of the electrofill modules 302, 304, or 306 or to one of the three separate modules 312, 314, and 316 configured for various process operations.

For example, the hand-off tool 346 may deliver the wafer substrate to the electrofill module 302 where a metal (e.g., copper) is plated onto the wafer substrate in accordance with implementations described herein. After the electroplating operation completes, the hand-off tool 346 may remove the wafer substrate from the electrofill module 302 and transport it to one of the PEMs, such as PEM 312. The PEM may clean, rinse, and/or dry the wafer substrate. Thereafter, the hand-off tool 346 may move the wafer substrate to another one of the PEMs, such as PEM 314. There, unwanted metal (e.g., copper) from some locations on the wafer substrate (e.g., the edge bevel region and the backside) may etched away by an etchant solution provided by chemical dilution module 322. The module 314 may also clean, rinse, and/or dry the wafer substrate.

After processing in the electrofill modules and/or the PEMs is complete, the hand-off tool 346 may retrieve the wafer from a module and return it to the cassette 342 or the cassette 344. A post electrofill anneal may be completed in the electrofill system 300 or in another tool. In one implementation, the post electrofill anneal is completed in one of the anneal stations 332. In some other implementations, dedicated annealing systems such as a furnace may be used. Then the cassettes can be provided to other systems such as a chemical mechanical polishing system for further processing.

Suitable semiconductor plating tools for implementing the above described methods include, without limitation, the SABRE® System and the SABRE® System 3D Lite manufactured by Novellus Systems of San Jose, Calif., the SLIM™ cell system manufactured by Applied Materials of Santa Clara, Calif., or the RAIDER™ tool manufactured by Semitool (part of Applied Materials) of Kalispell, Mont.

Figure 6:
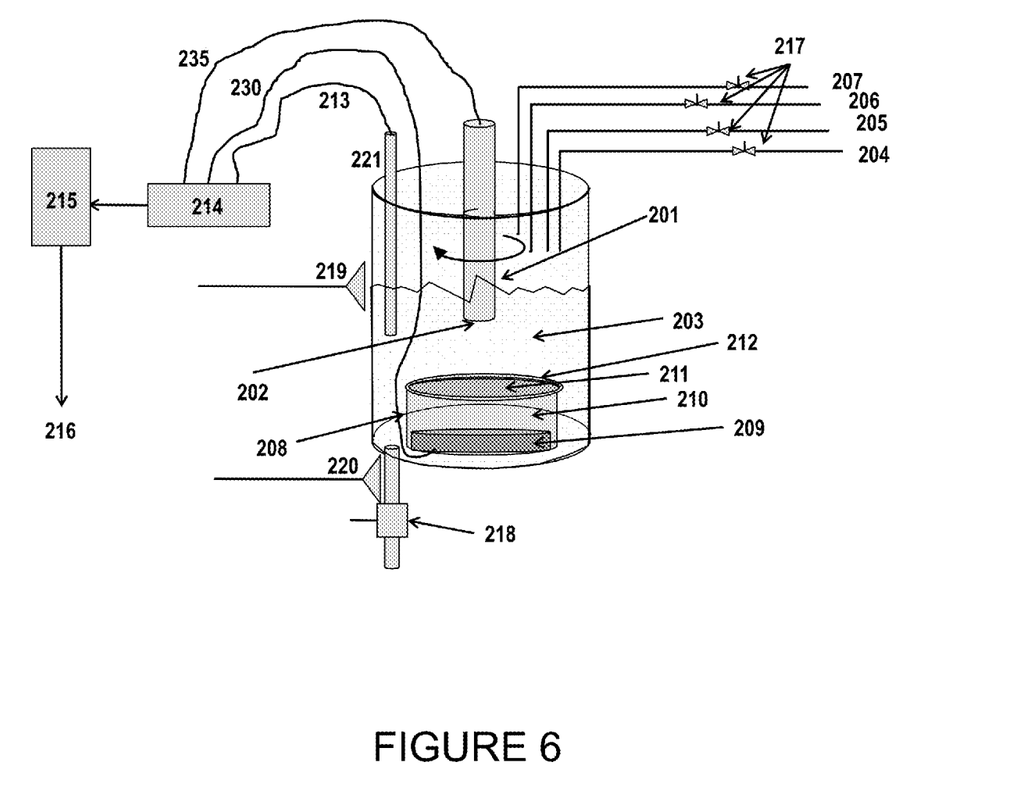
FIG. 6 shows an example of a cross sectional view of a metrology tool in accordance with certain embodiments presented herein.

FIG. 6 shows an exemplary metrology tool apparatus 200 according to the invention. In this example, the working electrode 201 for performing the electrochemical measurement is a rotating disk electrode composed of an outer cylindrical insulating material (e.g., plastic) surrounding a wire or rod for carrying current to the rotating disk surface 202. The disk surface 202 is often made of a noble metal such as platinum or gold. The various process fluids 203 used in the process (e.g., pre-plating solution, rinsing solution, activating solution, test bath solution and etching solution) are delivered by separate lines 204, 205, 206, 207, supplied by a pressurized and valve controlled (217) delivery, or by a set of syringe pumps (not shown). The level of processing fluid 203 in the container can be controlled by level sensing devices 219 and 220. Level sensing device 219 senses the fluid level in the metrology tool 200 to ensure that the tool sufficiently fills with fluid as needed, while level sensing device 220 operates to detect that the fluid in the tool is sufficiently drained as needed. The anode 209 (often made of copper when analyzing leveler in a copper plating solution) is contained in a separate sealed container 208 with a bottom, side walls and a membrane 211 (e.g. a cationic membrane such as Nafion) which keep the anode electrolyte solution 210 in the anode compartment 208. In this way, the anode electrolyte solution and the processing fluid are fluidically separated from one another both during plating and during the rinsing and draining of the various liquids. This separation is beneficial because the anode electrolyte solution is often free of additives which are present in the processing fluid, and because of the formation and transport of potentially interfering cuprous ions at the anode, and the reaction of the additive directly with the anode which is at an anodic potential vs. the cathode RDE can be inhibited A seal 212 around the periphery of the upper wall of the anode compartment 208 prevents transfer and leakage of fluid during all the various process steps, and addition and removal of fluids from the chamber. Electrical lead 230 carries current between the anode and the power supply and seals at the anode chamber 208. Electrical lead 235 carries current between the working electrode 201 and the power supply. Reference electrode 221 (vs. a Hg/HgSO$_4$ reference electrode) is also immersed in ionic communication with the electrolyte contained within the cell and electrically connected to the power supply via lead 213 (the power supply may be capable of continuously monitoring or controlling the voltage between the working electrode and the reference electrode). A drain and valve assembly 218 at the base of the cell container may be activated via a data collection and process controlling computer 215. The data collection computer 215, sometimes referred to as a controller, is in communication with and controls the programmable potentiostat/galvanostat 214 and sends results of the analysis for display and/or to a bath control and dosing apparatus on the tool (not shown) via communication line 216.

Certain embodiments include a controller that may serve various purposes. For example, the controller may be configured to cause various fluids to enter or exit a testing cell. These fluids may include, but are not limited to, pre-plating solution, pre-acceleration solution, rinsing solution, the plating solution to be tested, as well as the individual components in the solution to be tested, e.g., leveler, accelerator, suppressor, etc. The controller may be designed or configured to add these fluids at certain times or in response to sensed or calculated levels and/or component concentrations. In one embodiment, the controller is configured to add an amount of leveler to the plating solution where the concentration of leveler is determined to be too low. This configuration allows the plating solution to maintain a fairly uniform concentration of leveler over time. In certain embodiments, the controller is configured to perform (or cause to be performed) any or all of the operations described herein, including, for example, providing an electrode with a metal surface, exposing the electrode to a pre-acceleration solution, rinsing the electrode, measuring an electrochemical response while plating the electrode in a solution of unknown concentration, and/or determining the concentration of leveler based on the measured electrochemical response. In achieving these operations, the controller may be in communication with one or more of the elements described herein.

FURTHER IMPLEMENTATIONS

The apparatus/methods described hereinabove may be used in conjunction with lithographic patterning tools or processes, for example, for the fabrication or manufacture of semiconductor devices, displays, LEDs, photovoltaic panels and the like. Generally, though not necessarily, such tools/processes will be used or conducted together in a common fabrication facility. Lithographic patterning of a film generally comprises some or all of the following steps, each step enabled with a number of possible tools: (1) application of photoresist on a work piece, i.e., a substrate, using a spin-on or spray-on tool; (2) curing of photoresist using a hot plate or furnace or UV curing tool; (3) exposing the photoresist to visible, UV, or x-ray light with a tool such as a wafer stepper; (4) developing the resist so as to selectively remove resist and thereby pattern it using a tool such as a wet bench; (5) transferring the resist pattern into an underlying film or work piece by using a dry or plasma-assisted etching tool; and (6) removing the resist using a tool such as an RF or microwave plasma resist stripper.

It should also be noted that there are many alternative ways of implementing the disclosed methods and apparatuses. It is therefore intended that this disclosure be interpreted as including all such alterations, modifications, permutations, and substitute equivalents as fall within the true spirit and scope of the disclosed implementations.

What is claimed is:

1. A method of determining leveler concentration in a test solution, comprising:
   (a) providing an electrode having a metal surface;
   (b) exposing the electrode to a pre-acceleration solution comprising at least one accelerator compound and allowing the surface of the electrode to become substantially saturated with the at least one accelerator compound before removing the electrode from the pre-acceleration solution;
   (c) exposing the substantially saturated electrode to the test solution and measuring an electrochemical response while plating the substantially saturated electrode in the test solution, the test solution having an unknown concentration of leveler; and
   (d) determining the concentration of leveler in the test solution by comparing the electrochemical response obtained in operation (c) to a model relating leveler concentration to known electrochemical responses.

2. The method of claim 1, wherein the electrode is a rotating disk electrode.

3. The method of claim 2, wherein the rotating disk electrode rotates between about 100-5,000 rotations per minute during operation (c).

4. The method of claim 1, wherein the model in operation (d) is generated by performing operations (a)-(c) with solutions having known leveler concentrations.

5. The method of claim 1, wherein the electrochemical response is measured through galvanometric sweeping, stripping or AC impedance.

6. The method of claim 1, wherein operation (c) further comprises:
   (i) polarizing the substantially saturated electrode with a constant current; and
   (ii) measuring the substantially saturated electrode's potential over time.

7. The method of claim 1, wherein operation (c) further comprises:
   (i) polarizing the substantially saturated electrode with constant potential; and
   (ii) measuring the current to the substantially saturated electrode or the current density over time.

8. The method of claim 1, wherein the pre-acceleration solution comprises 0.05 to 10 g/L accelerator compound in deionized water or weak acid.

9. The method of claim 1, further comprising:
   applying a current to the electrode during operation (b), wherein the current density is greater than 5 mA/cm$^2$.

10. The method of claim 1, wherein a boundary layer thickness in the test solution near the substantially saturated electrode in operation is less than about 60 microns.

11. The method of claim 1, further comprising:
    regenerating the electrode to its starting condition.

12. The method of claim 1, wherein the method is performed outside a primary plating apparatus.

13. The method of claim 1, wherein the electrode is plated in a pre-plating solution comprising the same metal ions as those present in the test solution.

14. The method of claim 13, wherein the pre-plating solution does not contain any leveler species which are the same as a leveler species whose concentration is sought to be characterized in operation (d).

15. The method of claim 13, wherein the pre-plating solution does not contain any leveler.

16. The method of claim 1, wherein the method is repeated between 1 and 10 times per day per test solution.

17. The method of claim 1, further comprising:
    rinsing the substantially saturated electrode before operation (c) to remove unadsorbed accelerator compound.

18. A method of determining leveler concentration in a solution, comprising:
    (a) providing an electrode having a metal surface;
    (b) exposing the electrode to a pre-acceleration solution comprising at least one accelerator compound and allowing the surface of the electrode to become substantially saturated with the at least one accelerator compound;
    (c) providing a first solution with a known concentration of leveler and a second solution with an unknown concentration of leveler;
    (d) preparing a third solution by adding an amount of the second solution to the first solution;
    (e) measuring an electrochemical response while plating the electrode in the third solution;
    (f) determining the concentration of leveler in the third solution by comparing the electrochemical response obtained in operation (e) to a model relating leveler concentration to known electrochemical responses; and
    (g) determining the concentration of leveler in the second solution by relating the known concentration of leveler in the first solution, the determined concentration of leveler in the third solution and the amount of second solution added in operation (d).

19. The method of claim 18, wherein the second solution comprises a sample of solution taken from an electroplating apparatus.

20. The method of claim 18, wherein the concentration of leveler in the second solution is determined by a controller programmed with instructions to calculate the concentration of leveler in the second solution based on the concentration of leveler in the first solution, the amount of second solution added in operation (d) and the electrochemical response obtained in operation (e).

21. The method of claim 18, further comprising:
    rinsing the electrode before operation (c) to remove unadsorbed accelerator compound.

22. The method of claim 18, wherein two or more solutions used in the method are provided in different vessels.

23. The method of claim 22, wherein the vessels are provided on a conveyance mechanism.

24. The method of claim 22, wherein the vessels are stationary and the electrode is movable with respect to the vessels.

* * * * *